(12) United States Patent
Schmidt

(10) Patent No.: US 9,149,451 B1
(45) Date of Patent: *Oct. 6, 2015

(54) APPARATUS AND METHOD OF STIMULATING ELEVATION OF GLUTATHIONE LEVELS IN A SUBJECT

(71) Applicant: LifeWave, Inc., San Diego, CA (US)

(72) Inventor: David G. Schmidt, Poway, CA (US)

(73) Assignee: Lifewave, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/101,046

(22) Filed: Dec. 9, 2013

Related U.S. Application Data

(62) Division of application No. 12/121,674, filed on May 15, 2008, now Pat. No. 8,602,961.

(51) Int. Cl.
*A61K 31/198* (2006.01)

(52) U.S. Cl.
CPC .................................. *A61K 31/198* (2013.01)

(58) Field of Classification Search
CPC    A61K 2300/00; A61K 38/063; A61K 31/198
USPC ........... 424/449, 400, 468, 424, 444; 514/400
See application file for complete search history.

(56) References Cited

U.S. PATENT DOCUMENTS

| | | | |
|---|---|---|---|
| 3,658,070 A | 4/1972 | Diluzio | 131/267 |
| 4,746,508 A | 5/1988 | Carey et al. | 424/88 |
| 5,204,114 A | 4/1993 | Demopoulos et al. | 424/465 |
| 5,389,657 A | 2/1995 | Madsen | 514/369 |
| 5,393,350 A | 2/1995 | Schroeder | 136/205 |
| 5,597,976 A | 1/1997 | Schroeder | 136/205 |
| 5,618,823 A | 4/1997 | Cavalletti et al. | 514/283 |
| 5,651,973 A | 7/1997 | Moo-Young et al. | 424/401 |
| 5,738,624 A | 4/1998 | Zablotsky et al. | 600/9 |
| 5,837,281 A | 11/1998 | Iga et al. | 424/449 |
| 5,860,428 A | 1/1999 | Lesser et al. | 131/331 |
| 5,939,094 A | 8/1999 | Durif et al. | 424/448 |
| 6,030,950 A | 2/2000 | Ohlenschläger | 514/18 |
| 6,177,260 B1 | 1/2001 | Benzie et al. | 435/25 |

(Continued)

FOREIGN PATENT DOCUMENTS

EP    0 616 803 A2    9/1994

OTHER PUBLICATIONS

U.S. Appl. No. 10/075,221, filed Feb. 13, 2002, Blendermann.

(Continued)

*Primary Examiner* — Albert Navarro
*Assistant Examiner* — Ginny Portner
(74) *Attorney, Agent, or Firm* — Sheppard, Mullin, Richter & Hampton, LLP

(57) ABSTRACT

An apparatus configured to provide a beneficial biological effect for a subject, and/or a method of treating the subject using the apparatus. The apparatus may be configured to trigger and maintain the elevation of Glutathione levels within the subject. The apparatus may rely on a non-invasive mechanism to elevate Glutathione levels in the subject. The apparatus may not require a traditional power source such as a battery or wall plug in order to be effective in elevating Glutathione levels in the subject. To trigger and maintain the elevation of Glutathione levels within the subject, the apparatus may transmit communication to the body of the subject that results in increased levels of Glutathione within the subject.

6 Claims, 7 Drawing Sheets

(56) References Cited

U.S. PATENT DOCUMENTS

| | | | |
|---|---|---|---|
| 6,287,285 B1 | 9/2001 | Michal et al. | 604/264 |
| 6,407,133 B2* | 6/2002 | Hellstrand et al. | 514/400 |
| 6,475,514 B1 | 11/2002 | Blitzer et al. | 424/449 |
| 6,558,695 B2 | 5/2003 | Luo et al. | 424/449 |
| 6,617,306 B2 | 9/2003 | Stein et al. | 514/2 |
| 6,635,273 B1* | 10/2003 | Loscalzo et al. | 424/444 |
| 6,890,533 B2 | 5/2005 | Bomshteyn et al. | 424/179.1 |
| 6,890,553 B1 | 5/2005 | Sun et al. | 424/449 |
| 6,896,899 B2 | 5/2005 | Demopolos et al. | 424/451 |
| 7,125,387 B2 | 10/2006 | Kawabata et al. | 601/2 |
| 8,361,512 B2* | 1/2013 | Kaiser | 424/600 |
| 8,569,239 B2* | 10/2013 | Wang et al. | 514/17.7 |
| 8,602,961 B2* | 12/2013 | Schmidt | 600/15 |
| 8,734,316 B2* | 5/2014 | Schmidt | 600/15 |
| 8,802,730 B2* | 8/2014 | Sekhar | 514/562 |
| 8,828,955 B2* | 9/2014 | Ohto et al. | 514/33 |
| 2002/0061870 A1 | 5/2002 | Pearson et al. | 514/184 |
| 2002/0072501 A1 | 6/2002 | Cyr et al. | 514/23 |
| 2002/0148478 A1 | 10/2002 | Pera | 131/341 |
| 2002/0156340 A1 | 10/2002 | Blendermann | 600/15 |
| 2003/0031630 A1* | 2/2003 | Reznick et al. | 424/45 |
| 2003/0039697 A1 | 2/2003 | Zhao et al. | 424/486 |
| 2003/0055103 A1 | 3/2003 | Heinzen et al. | 514/456 |
| 2003/0099694 A1* | 5/2003 | Cevc et al. | 424/449 |
| 2003/0118615 A1 | 6/2003 | Blendermann | 424/400 |
| 2003/0147812 A1 | 8/2003 | Ueberle | 424/9.52 |
| 2003/0167556 A1 | 9/2003 | Kelley | 2/206 |
| 2004/0002461 A1* | 1/2004 | Matier et al. | 514/18 |
| 2004/0005306 A1* | 1/2004 | Loscalzo et al. | 424/94.1 |
| 2004/0057983 A1* | 3/2004 | Schmidt | 424/443 |
| 2004/0141949 A1* | 7/2004 | Rosenthal et al. | 424/85.1 |
| 2005/0032708 A1 | 2/2005 | Bush et al. | 514/18 |
| 2005/0059153 A1 | 3/2005 | George et al. | 435/446 |
| 2005/0123897 A1* | 6/2005 | Cevc et al. | 435/4 |
| 2005/0215871 A1 | 9/2005 | Feldman et al. | 600/309 |
| 2005/0271726 A1 | 12/2005 | Crum | 424/486 |
| 2006/0099244 A1 | 5/2006 | Guilford | 424/450 |
| 2006/0110474 A1 | 5/2006 | Asami | 424/757 |
| 2006/0208383 A1 | 9/2006 | Aisenbrey | 264/104 |
| 2007/0077258 A1 | 4/2007 | Guilford | 424/209.1 |
| 2008/0045448 A1* | 2/2008 | Vinitsky | 514/8 |
| 2008/0199400 A1 | 8/2008 | Dyer et al. | 424/9.1 |
| 2008/0208179 A1 | 8/2008 | Chan et al. | 606/9 |
| 2008/0220092 A1 | 9/2008 | Dipierro et al. | 424/649 |
| 2008/0260808 A1 | 10/2008 | Pinna et al. | 424/443 |
| 2010/0068279 A1 | 3/2010 | Hartwell | 424/486 |
| 2010/0099762 A1 | 4/2010 | Bush et al. | 514/546 |
| 2010/0117029 A1 | 5/2010 | Ying | 252/301.36 |
| 2010/0272662 A1 | 10/2010 | Bonte et al. | 424/64 |
| 2011/0184356 A1 | 7/2011 | Schmidt | 604/290 |
| 2012/0165596 A1 | 6/2012 | Schmidt | 600/15 |
| 2014/0276480 A1 | 9/2014 | Schmidt | 604/290 |

OTHER PUBLICATIONS

U.S. Appl. No. 10/302,527, filed Nov. 25, 2002, Blendermann.
U.S. Appl. No. 60/074,248, filed Feb. 10, 1998, Blendermann.
Albert Roy Davis and Walter C. Rawls, "Magnetism and Its Effect on the Living System", Apr. 1996, Acres USA Publications.
Kao, Mu-Jung, et al., "Effects of Infrared and Low-Power Laser Irradiation on Cell Viability, Glutathione and Glutathione-Related Enzyme Activities in Primary Rat Hepatocytes", *Journal of Formos Med. Assoc.*, vol. 102, No. 7, Jul. 2003, pp. 486-491.
Kawakita, Yasunori., et al., "Increase of Intracellular Glutathione by Low-Dose Gamma-Ray Irradiation is Mediated by Transcription Factor AP-1 in RAW 264.7 Cells", *Biol Pharm Bull*, vol. 26, No. 1, Jan. 26, 2003, pp. 19-23.
Schaffer, M., et al., "Magnetic Resonance Imaging (MRI) Controlled Outcome of Side Effects Caused by Ionizing Radiation, Treated with 780 nm-Diode Laser—Preliminary Results", *Journal of Photochemistry and Photobiology B: Biology*, vol. 59 (1-3), Dec. 2000, pp. 1-8.
Ball, Louise, et al., "Evidence for a Direct Link Between Glutathione Biosynthesis and Stress Defense Gene Expression in *Arabidopsis*", *The Plant Cell*, vol. 16, Sep. 2004, pp. 2448-2462.
Hamblin, Michael R., et al., "Mechanisms for Low Level Light Therapy", *Proc. of SPIE*, vol. 6140, 614001, 2006, pp. 1-12.
Paramas et al., "HPLC-Fluorimetric Method for Analysis of Amino Acid in Products of the Hive (Honey and Bee-Pollen)", *Food Chemistry*, vol. 95, 2006, pp. 148-156.
Miscellaneous Incoming Letter by Edward Blendermann, dated Jan. 9, 2013, and received by the U.S. Patent and Trademark Office on Jan. 14, 2013.
Objections to David Schmidt's Declaration by Edward Blendermann, dated Dec. 29, 2012, and received by the U.S. Patent and Trademark Office on Jan. 14, 2013.
Negrao et al., "Carnitine Supplementation and Depletion: Tissue Carnitines and Eznymes in Fatty Acid Oxidation", *The American Physiological Society*, 1987, 8 pages.

* cited by examiner

APPARATUS AND METHOD OF STIMULATING ELEVATION OF GLUTATHIONE LEVELS IN A SUBJECT

RELATED APPLICATIONS

This application is a divisional application of U.S. patent application Ser. No. 12/121,674, filed on May 15, 2008, now U.S. Pat. No. 8,602,961, issued Dec. 10, 2013, and this application is related to U.S. patent application Ser. No. 10/669,596, entitled "A Biomolecular Wearable Apparatus," the contents of each of which are hereby incorporated by reference into this disclosure in their entireties.

FIELD OF THE INVENTION

The invention relates to apparatuses and methods to non-invasively trigger and maintain biochemical changes in humans, for example by causing photobiomodulation effects within a human body to elevate human Glutathione levels.

BACKGROUND OF THE INVENTION

Blood Glutathione levels have been identified as being possible indicators of overall health. Glutathione, often referred to as the "master antioxidant" of the body, may have a range of diverse metabolic functions within the human body, including acting as a free radical scavenger, "recharging" depleted antioxidants back into their active state (Vitamin C, Vitamin E, Vitamin A, etc.), maintaining the immune system, supporting protein structures, promoting amino acid uptake by cells, synthesis and repair of DNA, detoxifying drugs and chemical toxins introduced to the body, removing heavy metals such as mercury, and/or other functions.

Conventional methodologies for elevating Glutathione levels include oral supplementation of Glutathione, oral supplementation of the amino acid Glutathione precursors, and use of nutritive substances that support enzymatic Glutathione production and injection of Glutathione. Each of these methods has draw backs. For example, it is known that Glutathione may be destroyed by stomach acids making oral supplementation ineffective. While oral supplementation of amino acid precursors and Glutathione enzyme cofactors may lead to blood Glutathione levels that are elevated by 10-40% after four weeks of use, these results tend to be unpredictable, and are time- and dose-dependent. These supplements include: whey protein, selenium, lipoic acid, NAC, glutamine, glycine, vitamin C, and Vitamin E. Further, the effectiveness of supplements to improve Glutathione levels may be dependent upon many factors including patient compliance, age, level of exposure to environmental toxins, and the need to ingest the supplements multiple times during the day in order to maintain adequate Glutathione levels.

Another conventional mechanism for elevating Glutathione levels is the injection of Glutathione. The injection of Glutathione tends to translate into a temporary elevation of Glutathione levels in the blood, however, this method may be unwieldy on a daily basis. This method may also be expensive and/or inconvenient, and because of the large size of the Glutathione molecule, the injected Glutathione may be unable to penetrate the cell membrane into the interior of the cell when administered in this form. In addition, blood sampling studies of individuals given intravenous Glutathione show that blood levels of Glutathione peak in 10 minutes and are back to the baseline in 30-60 minutes. As a result, although intravenous administration of Glutathione has been proven to be somewhat beneficial in clinical studies, its use may be impractical and/or ineffective for the general population.

Despite the relative inefficiency of conventional delivery mechanisms, treatments intended to result in elevated levels of Glutathione have been shown to be effective in a variety of settings. For example, both intravenous Glutathione therapy and the use of supplements that increase Glutathione levels have been shown to be effective in alleviating the symptoms of Parkinson's disease.

Glutathione levels have been shown to be reduced in diabetics and Glutathione metabolism is impaired by diabetes. Poorly controlled diabetics, who have depleted Glutathione, also show an evident impairment of glucose metabolism and a higher susceptibility to oxidative injury. In these subjects, the effect of exogenous Glutathione is more noticeable than in those with near-normal blood glucose. Treatments that increase Glutathione levels are also associated with better blood sugar control in diabetics as well as less diabetic complications. As a result, intravenous Glutathione is now being used as one method of treatment for diabetes.

As another example, intravenous Glutathione has been shown to be helpful in reducing exercise-related pain in individuals with peripheral artery disease.

Glutathione levels in the brain are reduced by use of thiomersal, a mercury containing substance placed in some vaccines. Some researchers believe that the acute depletion of Glutathione by mercury containing compounds in vaccines creates neurotoxicity. The severity of the illness may be related to the total amount of mercury received and the timeframe of the exposure. A number of studies have now confirmed that autistic children have reduced circulating levels of Glutathione in their blood stream and laboratory markers indicating increased oxidative stress. Tremendous controversy exists about this issue, with many doctors and parents now believing that vaccines containing this substance, along with other sources of mercury exposure, may cause autism. Both intravenous Glutathione therapy and oral antioxidant substances are widely used by many clinicians around the world in the treatment of autism because of the clinical results produced when these therapies are given. The reason Glutathione is used to treat mercury toxicity is because Glutathione is the major mechanism used by the liver, kidneys and brain to excrete mercury.

Medical literature demonstrates that various pharmaceutical chemicals and drugs deplete Glutathione levels in the body. In 1993 it was reported that 200-300 deaths occurred every year from acetaminophen poisoning in the UK. In the USA overdoses of prescription and nonprescription drugs containing acetaminophen results in more calls to poison control centers in the US than do overdoses of any other medication, accounting for more than 100,000 calls, as well as 56,000 emergency room visits, and 458 deaths due to acute liver failure per year. A report on the cases acute liver failure by the CDC between 2000 and 2004 determined that acetaminophen toxicity was the cause in 41% of adult cases of liver failure. The reason for the deaths from acute liver failure after acetaminophen overdose results from acute depletion of liver Glutathione levels. Glutathione is a critical antioxidant molecule involved in the detoxification of acetaminophen in the liver. If a person does not receive immediate treatment with Glutathione producing substances, the liver will fail and then the only other treatment is a liver transplant. The acute treatment of poisoning with this analgesic involves using antidotes such as intravenous infusions of N-acetylcysteine or alpha-lipoic acid, which are nutrients used by the body to produce Glutathione.

In 1977, Dr. Burton M. Berkson also discovered that alpha-lipoic acid, which generates Glutathione production in the liver, could also save the livers of individuals suffering from mushroom poisoning. Similarly, mild cases of liver toxicity are often treated with oral doses of N-acetylcysteine, alpha-lipoic acid or the essential amino acid methionine, which serve as substrates for Glutathione synthesis in the body.

In addition, the use of Glutathione promoting compounds, like alpha-lipoic acid along with silymarin and selenium, can be beneficial in some individuals suffering from viral hepatitis because of their ability to regenerate antioxidants and protect the liver from free-radical damage.

Drugs commonly used in anesthesia practice may create oxidative stress and Glutathione depletion in peripheral T cells. This supports Glutathione levels in individuals who are undergoing surgical procedures where anesthetic agents are used. In addition, maintaining Glutathione levels in individuals who are recovering from injuries and surgery is beneficial because of the positive response that Glutathione has on wound healing.

Glutathione may be beneficial in controlling side-effects associated with cancer therapies. For instance, non-prescription antioxidants and other nutrients may enhance the killing of therapeutic modalities for cancer, decrease their side effects, and protect normal tissue. Glutathione treatment has been shown to be an effective in reducing toxicity and side effects in individuals with ovarian cancer who are treated with cisplatin chemotherapy. More particularly, treatment with Glutathione has been shown to improve patients conditions with respect to depression, emesis, peripheral neurotoxicity, hair loss, shortness of breath and difficulty concentrating. As another example, many individuals will develop neurological symptoms when given chemotherapy agents. Some studies have shown that chemotherapy agents lower Glutathione levels in brain tissue and that the use of Glutathione can reduce brain toxicity, which may be associated with these neurological symptoms.

Another bodily system that appears to benefit from elevated Glutathione levels is the immune system. This may be in part because infections generally tend to deplete Glutathione levels in the body. The immune system works best if the lymphoid cells have adequate levels of Glutathione. Even small reductions in the intracellular Glutathione level may have effects on lymphocyte and immune functions. Rheumatoid arthritis and systemic lupus erythematosus are two chronic inflammatory conditions linked with the immune system, which have been associated with low levels of serum and erythrocyte Glutathione when compared to normal. Glutathione levels as measured by erythrocyte Glutathione are also low in the blood of individuals with osteoarthritis.

Glutathione is involved in T-cell activation low, and Glutathione could affect the outcome of the immune response during systemic diseases and aging. Because Glutathione depletion may occur in conjunction with sepsis, trauma, and shock, treatments that help maintain Glutathione levels may enhance immunocompetence and thus improve the ability of patients to recover from these and other critical illnesses.

Similarly, inflammation (e.g., due to infection and/or trauma) may suppress Glutathione levels, and/or present a variety of other health risks. For instance, when inflammation is prolonged, tissue damage, enhanced inflammatory mediator production, and suppressed lymphocyte function may occur as a consequence. In addition, chronic inflammation may predispose susceptible cells to undergo cancerous transformation. In general, the longer the inflammation persists, the higher the risk of cancer. Inflammatory processes may induce DNA mutations in cells via oxidative stress. DNA mutation and mitochondrial dysfunction occurs when the generation of free radicals in a system exceeds the system's antioxidant protection.

Reduced Glutathione levels have also been linked to various viral diseases. This may be at least in part because Glutathione levels tend to fall when a virus infects cells. Increasing the levels of Glutathione inhibits viral replication and can reduce viral load. Reduction of viral load with use of Glutathione has been seen in herpes infections, hepatitis viral infections, and HIV infections. Viral infections produce oxidative stress by depleting Glutathione levels. Clinical studies have indicated that antioxidant therapies that increase Glutathione can assist the body in dealing with infections. For example, Glutathione levels dramatically decrease in the first 24 hours after infection with human herpes simplex virus type 1 (HSV-1). Antioxidant molecules, such as GSH and N-acetylcysteine (NAC), have been demonstrated to inhibit viral replication. Similarly, antioxidant molecules to inhibit >99% the replication of HSV-1. Such inhibition may be concentration-dependent, not related to toxic effects on host cells and also maintained if the exogenous GSH is added as late as 24 hours after virus challenge, i.e., when virus infection has been fully established. As another example, N-acetylcysteine (NAC), a sulfur-containing amino acid antioxidant, appears to inhibit HIV replication by raising serum Glutathione levels through inhibition of TNF-a [Tumor Necrosis Factor]. In chronic hepatitis C, liver damage may be attributed to increased oxidative stress and Glutathione depletion. Use of therapies that increase Glutathione levels like NAC have shown clinical benefit.

An imbalance in oxidant/antioxidant levels in the cells and tissues is a major cause of cell damage and is the hallmark for lung inflammation. Glutathione is a vital protective antioxidant, which plays a key role in the control of inflammatory processes in the lungs. Oxidative stress is an important feature in the causation of chronic obstructive pulmonary disease. Controlling oxidative stress with antioxidants or boosting the endogenous levels of antioxidants such as Glutathione is likely to be beneficial in the treatment of chronic obstructive pulmonary disease.

The role of oxidative stress in acute pancreatitis has been evidenced indirectly by beneficial effects of antioxidants as well as directly by pancreatic Glutathione depletion and increased lipid peroxidation.

In burn patients, increased free radical production is paralleled by impaired antioxidant mechanisms, as indicated by burn-related decreases in superoxide dismutase, catalase, Glutathione, alpha tocopherol, and ascorbic acid levels. This supports the hypothesis that cellular oxidative stress is a critical step in burn-mediated injury, and suggests that antioxidant strategies designed to inhibit free radical formation and/or to scavenge free radicals may provide organ protection in patients with burn injury.

Acute strokes and acute myocardial infarctions create severe oxidative stress on the body. The body will initially respond adaptively by increasing the production of antioxidant enzymes like Glutathione in order to protect and preserve surviving tissues. This places severe demands on the production of antioxidants like Glutathione. If and when the demands overwhelm the production of endogenous antioxidants like Glutathione, antioxidant levels including Glutathione levels fall, and tissue damage becomes more severe. This may be particularly critical in the first week following an ischemic event when antioxidant enzyme concentrations are decreased below normal levels. Maintaining adequate levels of antioxidants in individuals with vascular disease and in individuals who have ischemic events can help reduce medical complications.

Glutathione levels fall with age, and older individuals in good health tend to have higher Glutathione levels. The reduction in antioxidant protection associated with reduced levels of Glutathione has been implicated in the increasing susceptibility to carcinogens, infections, disease, and drug sensitivity which occurs with advanced age.

During warfare, soldiers (and/or civilians) may be exposed to various toxic substances. Treatment intended to increase Glutathione levels may be beneficial to counteract the effects of these exposures. For example, organofluoride polymers are considered important and are used extensively in military vehicles such as tanks and aircraft. The occurrence of closed-space fires in such settings has led to toxicity studies of the resultant by-products created from incinerated organofluorines. Inhalation of a mixture of pyrolysis by-products of these substances produces a constellation of symptoms termed "polymer fume fever". Inhalation of this material may produce a "permeability" or "noncardiac" type of toxic pulmonary edema very much like that produced by phosgene. Animal studies suggest that increasing pulmonary concentrations of oxygen free-radical scavengers like Glutathione may be of value in counteracting these and other effects of this type of exposure. For example, N-acetyl cysteine has been found effective in increasing Glutathione levels. Similarly, effects of weaponized chemical agents, such as mustard gas, phosgene, and/or other agents, may be treated by elevating Glutathione levels.

Strenuous and prolonged exercise can deplete antioxidants including Glutathione in the body. Prolonged or repetitive aerobic activity causes the body to utilize large amounts of oxygen to produce ATP in the mitochondria. Unfortunately, oxygen utilization in the mitochondria also produces significant amounts of oxygen free radicals. A higher amount of exercise unavoidably produces larger amounts of free-radicals that must be neutralized by the body's antioxidant systems. The body can compensate for strenuous exercise by increasing antioxidant enzyme activity up to a point. However, prolonged, intensive and repetitive bouts of exhaustive exercise can eventually overwhelm the body's antioxidant reserves. When the antioxidant system begins to fail continuous oxidative stress can eventually overwhelm the protective mechanisms leading to impairment in cellular functions such as energy production and impairment of liver detoxification. Clinical research in animals has shown that when strenuous exercise is continued after Glutathione depletion has occurred, oxidative damage can be seen in the liver and endurance is significantly decreased. Physical exercise also may significantly increase total oxygen uptake by the body by 1000-2000%; however, oxygen flux in skeletal muscle fibers may increase by as much as 100- to 200-fold during exercise; generating massive amounts of reactive oxidant species.

If the generation of reactive oxygen species during physical exercise overwhelms tissue antioxidant defense systems then antioxidant levels may reach a state of depletion. Although an oxidant insult may lead to adaptive responses and strengthen antioxidant defenses in the heart and skeletal muscle tissue. Oxidative stress, however, can also lead to cardiac and skeletal muscle tissue damage in individuals who are not able to upregulate their antioxidant defense mechanisms. The levels of oxidized Glutathione rise during strenuous exercise, as Glutathione is used up in the tissues. Unless Glutathione is regenerated back to its active reduced state, free radicals will attack vulnerable cellular structures like cell membranes, which can be monitored by measuring the amount of lipid peroxidation in both blood and urine. Maintaining high blood Glutathione levels are associated with lower resting, and exercise-induced, lipid peroxidation. In humans, exercise-induced blood Glutathione oxidation is rapid and subject to control by antioxidant supplementation. Antioxidant supplementation is likely to provide beneficial effects against exercise-induced oxidative tissue damage.

Hearing loss due to exposure to high-levels of sound and noise is a problem for many people in all walks of life. People who listen to music with ear plugs, loud rock concerts, factory workers and military personnel are all subject to hearing loss due to high levels of sound and noise. Research has shown that noise and loud sounds will deplete Glutathione levels in ear cells and will lead to hearing loss and that therapies that maintain Glutathione functional levels in the ear cells will protect against hearing loss. One factor that has been identified is that exposure to noise will produce autotoxic free radicals, Glutathione depletion within the sensory hair cells, and Glutathione depletion in the bloodstream. The generation of free radicals by high-level noise and Glutathione depletion is thought to be one of the mechanisms involved in producing noise-induced-hearing-loss (NIHL).

Although sensory hair cells possess a natural antioxidant defense system involving Glutathione and Glutathione regenerating enzymes that neutralize free radicals, this system can become overwhelmed in extreme or chronic noise conditions or by exposure to certain types of drugs or toxins. Exposure to high-level noise and certain ototoxic drugs can damage cellular structures in sensory hair cells like cell membranes, proteins, mitochondria and DNA when the rate of generation of cytotoxic free radicals exceeds the neutralization capabilities of the antioxidant system. When the cell membrane is damaged, the cells cannot properly maintain their electrical potentials, nutrient entry, and toxin release. The cell membrane is primarily composed of phopholipids and sterols. These compounds are synthesized from precursors provided by the diet. Both cell membranes and cell organelles are often damaged by oxidative processes and need continual protection from antioxidant defenses and a continual source of cellular energy, which is obtained from high-energy phosphates produced by metabolic energy pathways. Metabolic and antioxidant pathways operate through membrane-associated enzymes that require nutrient precursors and vitamin and mineral enzyme activators.

Other benefits may be associated with enhanced levels of Glutathione.

SUMMARY OF THE INVENTION

One aspect of the invention relates to apparatuses and methods to trigger biochemical changes in humans to elevate Glutathione levels and/or maintain elevated Glutathione levels without the introduction of external chemicals or solid objects into the body. For example, the trigger may be effected by causing photobiomodulation effects through regulation of the human thermodynamic energy-flow within a human body.

According to one embodiment, the invention relates to a wearable apparatus that may include components (detailed below) for directing specific wavelengths of light (e.g., in the infrared, visible and/or ultraviolet regions) into the body for the purpose of producing a desired photobiomodulation effect in humans. In some implementations, the electromagnetic radiation may be polarized (e.g., linearly, circularly, elliptically, or otherwise).

According to another embodiment, the invention relates to a wearable apparatus that may include biomolecular components having orthomolecular and/or non-orthomolecular organic materials which are capable of optical levororotary action. The biomolecular components may include, for example, stereoisomers having a left-handed chirality. Other components may be used.

According to another embodiment, the invention relates to a wearable apparatus that may include components that emanate specific wavelengths of light (e.g., in the infrared, visible and/or ultraviolet regions) that is directed onto the skin of a subject. This can produce a photobiomodulation effect in humans to trigger elevated Glutathione levels that can be maintained at least while the apparatus is held proximate to the subject.

According to one embodiment the apparatus may be configured to non-invasively trigger and maintain the elevation of Glutathione levels within a subject. The triggering may be caused by directing electromagnetic radiation into the body of the subject at a wavelength and/or wavelengths that cause levels of Glutathione within the body of the subject to rise. The maintenance of the elevated levels may be caused by maintaining proximity of the apparatus with the subject over a period of time. Advantageously, the apparatus may not require a traditional power source, such as a battery or wall plug, in order to be effective. Rather, to trigger and maintain the elevation of Glutathione levels within the subject, the apparatus may reflect electromagnetic radiation generated by the body of the subject (e.g., infrared radiation) and/or may receive electromagnetic radiation generated by the body of the subject and implement the energy of the received electromagnetic radiation to generate electromagnetic radiation that is transmitted back onto the skin of the subject. This electromagnetic radiation may be transmitted to cells in the body, for example through one or more collagen matrices within the body. At least certain ones of the receiving cells may be prompted by the electromagnetic radiation to increase production of Glutathione.

Since reduced Glutathione levels appear to be a cause and/or symptom of several health conditions, the subject may be treated for one or more of these health conditions with the apparatus. Elevated Glutathione levels appear to provide one or more health benefits. As such, treatment of the subject with the apparatus may provide one or more of these health benefits to the subject.

In some implementations, the apparatus may include one or more substrates, a chemical mixture, an enclosure, and/or other components (some examples of which are described herein). The substrate may provide a base material on which the chemical mixture is disposed. For example, the substrate may be formed from a fabric or other sheet material that is saturated with the chemical mixture. The chemical mixture may include one or more compounds that, when brought in proximity to the body of the subject, trigger and maintain the elevation of Glutathione levels in the subject. The chemical mixture may trigger and maintain the elevation of Glutathione levels in the subject without coming into direct contact with the subject or entering the body. The enclosure may surround the substrate and the chemical mixture. The enclosure may impede, or even prevent contamination from the environment of the apparatus from coming into contact with the substrate and the chemical mixture enclosed therein. In addition to preventing contamination of the chemical mixture, the isolation of the substrate and the chemical mixture by the enclosure may prevent one or more constituents of the chemical mixture from being evaporated and/or otherwise drawn out of the enclosure.

The chemical mixture may trigger and maintain the elevation of Glutathione levels by providing communication to the body of the subject that causes the body of the subject to increase levels of Glutathione. The communication may be emanate from one or more solutions and/or solids within the chemical mixture. The communication may include electromagnetic radiation and/or a magnetic field that emanate from the chemical mixture. The electromagnetic radiation may emanate from the chemical mixture in the infrared spectrum. The electromagnetic radiation may include electromagnetic radiation (e.g., UV, visible, IR, etc.) that is generated by the body of the subject and is reflected back into the body of the subject (at certain wavelengths) by the chemical mixture. The electromagnetic radiation may include electromagnetic radiation that is generated by the chemical mixture. The chemical mixture may reflect obtain the energy to generate the electromagnetic radiation from electromagnetic radiation received from the body of the subject in the form of infrared radiation (e.g., heat generated by the body of the subject). To generate a magnetic field, the chemical mixture may act as a magnetic pole by virtue of the composition and/or structure of the molecules within the chemical mixture.

The electromagnetic radiation may be reflected by, and/or generated from within, the chemical mixture at a wavelength (or wavelengths) and/or intensity that, when received in the body of the subject, triggers and maintains the elevation of Glutathione levels within the body of the subject. For example, the received electromagnetic radiation may constitute signals for cells within the body of the subject to increase the amount of Glutathione that is produced within the body of the subject.

The above-described mechanism of operation of the chemical mixture in triggering and maintaining the elevation of Glutathione levels within the patient should not be viewed as limiting. Other mechanisms for elevating Glutathione levels within subjects in response to being brought into proximity with the chemical mixture can be within the scope of the invention. One or more other mechanisms may be effective in triggering and maintaining the elevation in Glutathione levels experienced by subjects brought into proximity with the chemical mixture, and any such mechanisms are included within the scope of this disclosure.

In some implementations, the chemical mixture may include one or more natural amino acids. The one or more natural amino acids may include at least one amino acid that is at least partially dissolved within a fluid, such as water. The one or more natural amino acids may include at least one amino acid that is at least partially in solid form. The at least one solid natural amino acid may be suspended within a fluid, such as water, and/or may be carried by a binder, such as latex rubber, silicone rubber, epoxy, wax, and/or some other binder. In some instances, the one or more natural amino acids may include Glutathione.

As used herein, the term "natural amino acid" may include amino acids having a chirality (e.g., "left-handed") that enables inclusion within peptides and/or polypeptides that form the basic structured units of proteins and/or other natural amino acids.

According to various implementations, the apparatus may include a mechanism that holds the enclosure in place at or near the skin of the subject. In some implementations, the mechanism may include an adhesive, such as a medical grade adhesive, that removably adheres to the skin of the subject. Other adhesives and/or sources of adhesion may be used. In some instances, the adhesive of the mechanism may be applied directly to the enclosure to form an adhesive patch that can be applied to the skin of the subject. In some instances, the adhesive of the mechanism may be applied to a film that is separate from the enclosure, and the enclosure may be fixedly attached to the film (e.g., via an adhesive or laminate) to form the adhesive patch.

While the apparatus is installed on the subject with the adhesive removably adhereing to the subject at or near the skin, the enclosure may prevent direct contact between the subject and the substrate and/or the chemical mixture. Nonetheless, due to the non-invasive nature of the operation of the apparatus in triggering and maintaining elevated levels of Glutathione in the subject, the proximity of the apparatus to the subject may result in elevated levels of Glutathione within the subject. As such, the apparatus may be "non-transdermal" in that no chemicals are necessarily introduced to the skin of the subject to provide the desired result of treatment (e.g., the elevation of Glutathione levels).

Although during treatment, the apparatus may be placed at or near the subject, a variety of mechanisms that hold the enclosure in place at or near the skin of the subject may be implemented in place of the adhesive described above. For example, a band (for receiving an extremity of the subject) a ring, a piece of jewelry, an item of clothing, a hat, and/or other mechanisms for retaining the enclosure containing the substrate and the chemical mixture at or near the subject may be implemented.

Treatment

As has been enumerated above, depleted Glutathione levels are a cause and/or symptom of various ailments. These ailments include conditions linked with elevated levels of mercury within the body, diabetes, degenerative brain conditions (e.g., Parkinson's disease), peripheral artery disease, autism, liver toxicity, sepsis, viral infection (e.g., herpes, hepatitis, HIV, etc.), pulmonary disease, acute pancreatitis, burn injuries, auto-immune dysfunction (e.g., rheumatoid arthritis, lupus, etc.), osteoarthritis, stroke, heart attack, and/or other ailments. As a result, the scope of this disclosure encompasses a method of treating a subject suffering from one or more of these ailments with the apparatus. The treatment, which would result in an elevation in the levels of Glutathione within the subject by a therapeutically effective amount, among other things, may include affixing the apparatus to the subject such that the apparatus remains at or near the skin of the subject for a prolonged period of time.

Similarly, Glutathione levels may be depressed by various medical treatments designed to treat an affliction of the subject. For example, treatments that may depress Glutathione levels may include pain medications such as acetaminophen, anesthetic pharmaceuticals, cancer treatments (e.g., chemotherapy, radiation therapy, etc.), and/or other treatments. As a result, the scope of this disclosure encompasses a method of treating a subject having received another medical treatment, the effects of which include depressed Glutathione levels, with the apparatus. The treatment, which would result in an elevation in the levels of Glutathione within the subject by a therapeutically effective amount, among other things, may include affixing the apparatus to the subject such that the apparatus remains at or near the skin of the subject for a prolonged period of time.

Another cause of reduced Glutathione levels within an individual includes exposure to chemical agents present at times during warfare. These chemical agents may include weaponized chemical agents (e.g., Mustard gas, phosgene, etc.), chemical agents produced during the operation of machinery for the purposes of warfare (e.g., organofluoride polymers, etc.), and/or other chemical agents. Accordingly, the scope of this disclosure encompasses a method of treating a subject having been exposed to one or more chemical agents during the course of warfare, the effects of which include depressed Glutathione levels, with the apparatus. The treatment, which would result in an elevation in the levels of Glutathione within the subject by a therapeutically effective amount, among other things, may include affixing the apparatus to the subject such that the apparatus remains at or near the skin of the subject for a prolonged period of time.

The elevation of Glutathione levels within the subject may enhance the health of individuals in a variety of circumstances outside of those enumerated immediately above. For example, the elevation of Glutathione levels may be of benefit to the subject in recovering from exercise, dealing with exposure to loud and/or prolonged noise, aging, and/or other circumstances. Accordingly, the scope of this disclosure encompasses a method of treating a subject experiencing one or more circumstances that tend to decrease the overall health of the subject with the apparatus. The treatment, which would result in an elevation in the levels of Glutathione within the subject by a therapeutically effective amount, among other things, may include affixing the apparatus to the subject such that the apparatus remains at or near the skin of the subject for a prolonged period of time.

The amount of time for which the apparatus may remain proximate to a subject ("treatment time") and/or the frequency with which the apparatuses are applied ("treatment frequency") may depend on one or more parameters, such as, for example, a Glutathione mediated disorder being treated, a sensitivity of the subject to the apparatus, a number of apparatuses applied to the subject, and/or other parameters. For example, to elevate Glutathione levels by a therapeutically beneficial level to combat toxicity (e.g., elevated mercury levels), the apparatus may be provided proximate to the subject for a treatment time of between 1 hour and 12 hours and at a treatment frequency of every day or every other day. As another example, to elevate Glutathione levels by a therapeutically beneficial level to act as a prophylactic against chemicals encountered by soldiers during combat (e.g., chemical weapons, weapons discharge, etc.), the apparatus may be applied to the subject substantially continuously. As another example, to elevate Glutathione levels by a therapeutically beneficial level in a subject suffering from an inflammatory condition, the apparatus may be applied to the subject for a treatment time of between about 8 hours and about 12 hours and with a treatment frequency of approximately 1 day. Other treatment times and treatment frequencies may be used depending on the relevant parameters.

Locations

According to various implementations of one or more of the methods of treatment described above, affixing the apparatus to the subject may include affixing the apparatus to the subject such that the chemical mixture and/or substrate within the enclosure are held proximate to one or more predetermined locations on the subject. For example, the one or more predetermined locations on the subject may include one or more positions on the body of the subject that have a positive electrical potential. The one or more predetermined locations on the subject may include one or more acupuncture points, such as, for instance, one or more Yang points. In some implementations, the one or more predetermined locations comprise the palm side of the right forearm of the subject, the chest of the subject, under the navel of the subject, and/or other locations on the body of the subject. In some implementations, a plurality of apparatuses may be applied to different locations on the body of the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
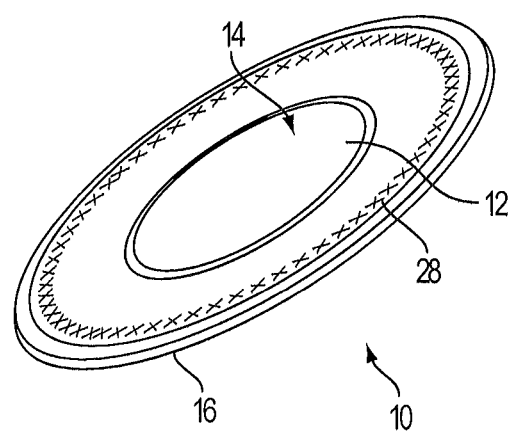
FIG. 1 illustrates an apparatus, according to one or more embodiments of the invention.

FIG. 1 illustrates an apparatus 10 configured to provide a beneficial biological effect for a subject (for example, triggering and maintaining the elevation of Glutathione levels within the subject). Apparatus 10 may trigger and maintain the elevation of Glutathione levels within the subject in a non-invasive (non-transdermal) and unpowered (without requiring a conventional external power source) manner. To trigger the elevation of Glutathione levels within the subject, apparatus 10 may transmit communication to the body of the subject that result in increased levels of Glutathione within the subject. This communication may include one or both of electromagnetic radiation and/or a magnetic field that emanate from apparatus 10. To maintain elevated levels of Glutathione in the subject, apparatus 10 may be held in proximity with the subject for an extended period of time. Apparatus 10 may be implemented to provide treatment to the subject for one or more conditions in which a presence of an enhanced level of Glutathione may be beneficial. In some implementations, apparatus 10 may include a substrate 12, a chemical mixture 14, an enclosure 16, and/or other components.

In some implementations, substrate 12 may be formed from a fabric or other sheet material. For example, substrate 12 may be formed from a polyester and/or cotton fabric sheet material. As another example, substrate 12 may be formed from a polyethylene fabric. In some instances, substrate 12 may include a commercially available polyester and/or cotton fabric sheet material, such as a 100% polyester fabric material available from Pellon®, a 100% cotton fabric material available from Pellon®, or a cotton/polyester blend fabric material available from Pellon®. The material of substrate 12 may be selected so as not to react with chemical mixture 14. In certain implementations, apparatus 10 may include a plurality of substrates 12.

It has bee found that the size of substrate 12 and apparatus 10 may have limited impact on the ability of the apparatus 10 to maintain an elevated level of Glutathione within a subject. Accordingly, the size of substrate 12 and apparatus 10 may be formed with an unobtrusive size when applied to the skin of a subject, yet still being large enough to be handled and applied with relative ease. Further, the size of substrate 12 and apparatus 10 may be tailored to an intended application. For example, an embodiment of apparatus 10 designed to be applied to an earlobe of a subject may be smaller than an embodiment of apparatus 10 designed to applied to the inner arm of the subject. Although the size of apparatus 10 and/or substrate 12 may vary, in some instances, substrate 12 may be formed having a length and/or width of about 1 inch, or having a diameter of about 1 inch.

According to various implementations, chemical mixture 14 may include one or more compounds that, when brought in proximity to the body of the subject, trigger and maintain the elevation of Glutathione levels in the subject. In some implementations, chemical mixture 14 may include one or more natural amino acids. The one or more natural amino acids may include at least one amino acid that is at least partially dissolved within a fluid, such as water. The one or more natural amino acids may include at least one amino acid that is at least partially in solid form. The one or more natural amino acids may include Glutathione. The at least one solid natural amino acid may be suspended within a fluid, such as water, and/or may be carried by a binder, such as latex rubber, silicone rubber, epoxy, wax, and/or some other binder.

In certain implementations, chemical mixture 14 may include one or more additives. The one or more additives may include one or more of glycerin, propylparaben, potassium sorbate, methylparaben, Colloidal Gold, aloe vera, powdered jade, and/or other additives. For example, glycerin may combat decomposition of chemical mixture 14 due to heat during storage, and/or may provide a protection against bacteria or fungus. Similarly, propylparaben, potassium sorbate, methylparaben, and/or Colloidal Gold may provide anti-bacterial protection for chemical mixture 14, while aloe vera may protect against decomposition caused by heat during storage. The amounts of such elements to be added to chemical mixture 14 may be determined by one of ordinary skill in the art according to the known properties of these additive chemical elements.

In some implementations, chemical mixture 14 may include generally equal parts of L-Glutathione and one or more other natural amino acids (e.g., L-Carnitine, L-Camintine, etc.). However, this is not intended to be limiting, as the proportion Glutathione to the one or more other natural amino acids with precision has been found to not be especially impactful to the operation of apparatus 10. The Glutathione and the one or more other natural amino acids may be suspended in water. The concentration of the Glutathione/natural amino acid mixture may not substantially impact the amount by which apparatus 10 maintains elevated Glutathione within a subject. However, if the concentration is too low, the L-Glutathione/natural amino acid mixture may be decomposed by ambient heat during storage. Although the addition of one or more of the additives discussed above (e.g., glycerin) may combat such decomposition.

In some implementations, the solution of L-Glutathione/natural amino acid mixture in apparatus 10 may include between about 10 mg and about 1000 mg of each of L-Glutathione and some other natural amino acid (e.g., L-Carnitine). In some implementations, the solution of L-Glutathion/natural amino acid mixture in apparatus 10 may include between about 100 mg and about 900 mg each of L-Glutathione and some other natural amino acid. In some implementations, the solution of L-Glutathion/natural amino acid mixture in apparatus 10 may include between about 250 mg and about 750 mg each of L-Glutathione and some other natural amino acid. In some implementations, the solution of L-Glutathion/natural amino acid mixture in apparatus 10 may include about 500 mg each of L-Glutathione and some other natural amino acid. In some implementations, the solution of L-Glutathion/natural amino acid mixture in apparatus 10 may include between about 1 mL and about 50 mL of water. In some implementations, the solution of L-Glutathion/natural amino acid mixture in apparatus 10 may include between about 5 mL and about 40 mL of water. In some implementations, the solution of L-Glutathion/natural amino acid mixture in apparatus 10 may include between about 10 mL and about 30 mL of water. In some implementations, the solution of L-Glutathion/natural amino acid mixture in apparatus 10 may include about 15 mL of water.

As used herein, the term "water" may refer to one or more forms of water. For example, "water" may refer to distilled water, tap water, altered structure water, ionized water, de-ionized water, filtered water, and/or other forms of water.

Purely by way of illustration, one implementation of chemical mixture 14 may be produced, for example, by combining 2 gallons of water, 50 grams of a natural amino acid (or natural amino acids) such as L-Carnitine, L-Camintine, and/or other natural amino acids, 10 grams of L-Glutathione, 1 gallon of aloe vera (e.g., in liquid form), 90 grams of potassium sorbate, 190 ounces of glycerin (e.g., vegetable glycerin), and/or other components.

Chemical mixture 14 may trigger and maintain the elevation of Glutathione levels in the subject without coming into direct contact with the subject. It is believed that chemical mixture 14 may trigger and maintain the elevation of Glutathione levels by transmitting communication to the subject. The communication may be emanate from one or more solutions and/or solids within chemical mixture 14. The communication may include electromagnetic radiation and/or a magnetic field that emanate from chemical mixture 14. The electromagnetic radiation may include radiation in the infrared spectrum. The electromagnetic radiation may include electromagnetic radiation that (e.g., UV, visible, IR, etc.) that is generated by the body of the subject, and is reflected by chemical mixture 14 (e.g., at the spectral infrared signature of Glutathione) back into the body of the subject. Chemical mixture 14 may obtain the energy to generate some or all of the electromagnetic radiation from electromagnetic radiation received from the body of the subject in the form of infrared radiation (e.g., heat generated by the body of the subject).

More particularly, according to various implementations, it is believed that after manufacture, chemical mixture 14 includes one or more solid formations, such as crystals, carried on substrate 12. When placed in proximity to the body of the subject, it is believed that infrared electromagnetic radiation emitted by the body of the subject in the form of body heat may be received by chemical mixture 14, and that the energy carried by the body heat of the subject may energize the solid formations within chemical mixture 14 (and/or other constituents within chemical mixture 14) in such a manner that chemical mixture 14 may emit electromagnetic radiation therefrom. For example, the energy carried by the infrared electromagnetic radiation generated by the subject may cause the solid formations within chemical mixture 14 to oscillate with a resonance such that electromagnetic radiation is generated at certain wavelengths from the oscillation (e.g., one or more of the certain wavelengths may be common to the spectral infrared signature of Glutathione). The electromagnetic radiation generated from the oscillation of the solid formations within chemical mixture 14 may be received back into the body of the subject.

It is believed that the electromagnetic radiation emanating from chemical mixture 14 at a frequency (or frequencies) and/or intensity that, when received in the body of the subject, triggers and maintains the elevation of Glutathione levels within the body of the subject. For example, the electromagnetic radiation emanating from chemical mixture 14 may be directed to the skin, and may travel from the skin through by body (e.g., via one or more collagen matrices within the body) to cells within the body of the subject. These cells may be responsive to the electromagnetic radiation emanating from chemical mixture 14 such that the cells increase the amount of Glutathione that is produced within the body of the subject. The mechanism that triggers and maintains this increased amount of Glutathione may be similar to the mechanism that triggers and maintains the production of vitamin D by cells in response to exposure to certain wavelengths of electromagnetic radiation in the UV spectrum.

The above-described mechanism of operation of chemical mixture 14 in triggering and maintaining the elevation of Glutathione levels within the patient should not be viewed as limiting. Other mechanisms for elevating Glutathione levels within subjects in response to being brought in proximity with chemical mixture 14 can be within the scope of the invention. One or more other such mechanisms may be effective in triggering and/or maintaining the elevation in Glutathione levels experienced by subjects brought into proximity with chemical mixture 14, and any such mechanisms are included within the scope of this disclosure.

In some implementations, enclosure 16 may surround substrate 12 and chemical mixture 14. Enclosure 16 may impede, or even prevent contamination from the environment of apparatus 10 from coming into contact with substrate 12 and chemical mixture 14 enclosed therein. For example, enclosure 16 may form a barrier around substrate 12 and chemical mixture 14 that seals substrate 12 and chemical mixture 14 from atmosphere and holds substrate 12 and chemical mixture 14 in isolation. In addition to preventing contamination of chemical mixture 14, the isolation of substrate 12 and chemical mixture 14 by enclosure 16 may prevent one or more constituents of chemical mixture 14 from being evaporated and/or otherwise drawn out of enclosure 16.

In some implementations, enclosure 16 may be formed from a flexible, relatively rugged material capable of isolating substrate 12 and chemical mixture 14. For example, enclosure 16 may be formed, at least in part, from one or more of a polyester film, a plastic film (e.g., polyethylene, polypropylene, ABS, plexiglass, lexan, PVC, etc.) and/or other materials. In some instances, the material implemented to form enclosure 16 may polarize electromagnetic radiation in a predetermined manner.

In some implementations, apparatus 10 may include one or more substances other than the chemicals included within chemical mixture 14 that have infrared reflection spectra conducive to the operation of apparatus 10. For example, carbon fibers, jade, certain ceramic materials, and/or other materials having infrared reflection spectra similar to the infrared emission spectra of the human body may be incorporated into apparatus 10. Such materials may be included integrally into the material of enclosure 16, some or all of enclosure 16 itself may be formed from such materials, such materials may be disposed inside of enclosure 16 with chemical mixture and substrate 12, some or all of substrate 12 may be formed from such materials, a layer of such materials may be provided externally to enclosure 16, and/or such materials may be incorporated into apparatus 10 in other ways.

Figure 2A:
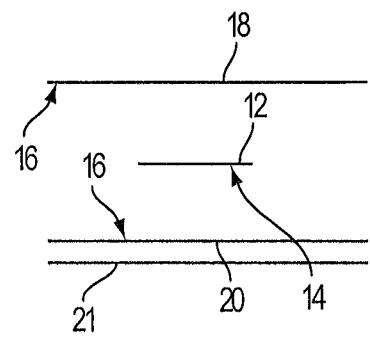
FIGS. 2(A) and 2(B) illustrate an apparatus, according to one or more embodiments of the invention.
Figure 2B:
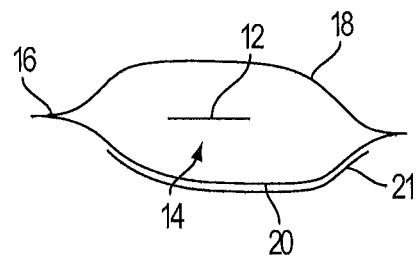

According to some implementations, enclosure 16 may be formed from two separate pieces of material. For example, FIG. 2A illustrates the manufacture of apparatus 10 where enclosure 16 is formed from a first piece of material 18 and a second piece of material 20. Between pieces 18 and 20, substrate 12 is disposed, having been previously saturated with chemical mixture 14. With substrate 12 disposed therebetween, the periphery of pieces 18 and 20 are laminated together, thereby forming enclosure 16 surrounding substrate 12 and chemical mixture 14, as illustrated in FIG. 2B. For example, pieces 18 and 20 may be formed from a thermal laminating film, and the periphery of pieces 18 and 20 may be exposed to an elevated heat and/or pressure to form enclosure 16.

In some implementations, apparatus 10 may include another layer 21 disposed on one or both sides of enclosure 16. Layer 21 may be provided to process electromagnetic radiation emanating from chemical mixture 14 (e.g., by polarizing the electromagnetic radiation, by filtering the electromagnetic radiation, etc.). Layer 21 may be formed from one or more materials with a reflection spectra (e.g., an infrared reflection spectra) that facilitates the operation of apparatus 10.

Figure 3A:
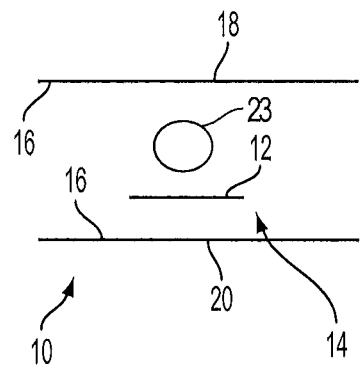
FIGS. 3(A) and 3(B) illustrate an apparatus, according to one or more embodiments of the invention.
Figure 3B:
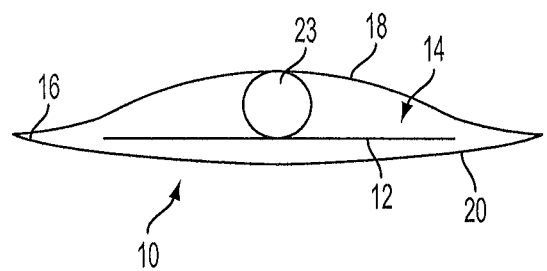

Referring to FIGS. 3A and 3B, in some implementations, an object 23 may be included within enclosure 16. Object 23 may include a bead intended to apply a pressure to the skin of the subject when apparatus 10 is applied to the subject. The bead may be formed from a medical grade plastic, or some other material. If apparatus 10 is applied at an acupuncture point on subject, the pressure applied by object 23 may be received by the subject at the acupuncture point, which may provide apparatus 10 with an additional therapeutic impact on the subject. In some implementations, object 23 may include one or more magnets. Such magnets may have a therapeutic value for the subject.

Figure 4A:
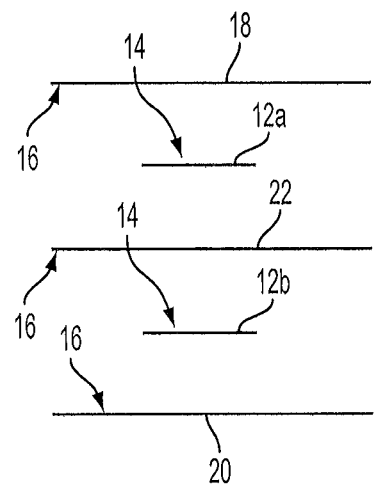
FIG. 4(A) illustrates an apparatus prior to assembly.
Figure 4B:
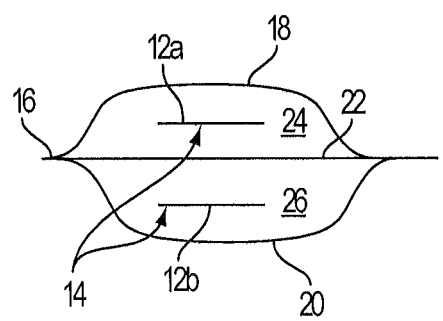
FIG. 4(B) illustrates an apparatus after assembly, according to one or more embodiments of the invention.

Although apparatus 10 has been shown in FIGS. 1 and 2 A-B and described above as including a single substrate 12, this is not intended to be limiting. For example, FIG. 4A illustrate one or more implementations of apparatus 10 prior to assembly in which apparatus 10 includes two substrates 12 (illustrated in FIG. 4 as substrate 12a and substrate 12b). FIG. 4B illustrates apparatus 10 shown in FIG. 4A after assembly. In the implementations illustrated in FIGS. 4A and 4B, enclosure 16 includes an additional piece of material 22, and forms two separate spaces 24 and 26, with each space 24 and 26 accommodating a separate one of substrates 12a and 12b. Additional piece 22 may be formed from the same material as pieces 18 and 20, and may maintain spaces 24 and 26 in sealed isolation from each other. As an alternative, additional piece 22 may be formed from a material that is permeable to chemical mixture 14, and/or additional piece 22 may form passages between spaces 24 and 26. In these instances, chemical mixture 14 may circulate between spaces 24 and 26. It should be appreciated that the scope of this disclosure includes implementations that include more than two substrates, and/or implementations in which two or more of the substrates are not separated by a piece of material such as additional piece of material 22.

In some implementations in which apparatus 10 includes multiple substrates, such as substrates 12a and 12b illustrated in FIGS. 4A and 4B, during manufacture, all of the substrates may be saturated with the same chemical mixture. In other implementations, individual ones of the substrates may be saturated with different chemical mixtures. For example, in the implementations illustrated in FIGS. 4A and 4B, during manufacture, substrate 12a may be saturated with a first chemical mixture 14a and substrate 12b may be saturated with a second chemical mixture 14b. By way of non-limiting example, first chemical mixture 14a may include a first set of one or more natural amino acids, such as L-Arginine for example, and second chemical mixture 14b may include a second set of one or more natural amino acids, such as L-Glutathione.

Referring back to FIG. 1, according to various implementations, apparatus 10 may include a mechanism 28 that holds enclosure 16 in place at or near the skin of the subject. In some implementations, mechanism 28 may include an adhesive, such as a medical grade adhesive, that removably adheres to the skin of the subject. In some instances, the adhesive of mechanism 28 may be directly to enclosure 16 to form an adhesive patch that can be applied to the skin of the subject. In some instances, the adhesive of mechanism 28 may be applied to a film 30 that is separate from enclosure 16, and enclosure 16 may be permanently attached to film 30 (e.g., via an adhesive or laminate) to form the adhesive patch.

From the foregoing, it should be appreciated that in some implementations, while apparatus 10 is installed on the subject with the adhesive of mechanism 28 removably adhereing to the subject at or near the skin, enclosure 16 may prevent direct contact between the subject and substrate 12 and/or chemical mixture 14. Nonetheless, due to the non-invasive nature of the operation of apparatus 10 in triggering and maintaining elevated levels of Glutathione in the subject, the proximity of apparatus 10 to the subject may result in elevated levels of Glutathione within the subject. As such, apparatus 10 is non-transdermal and non-invasive in that no chemicals or solid objects are introduced to the skin of the subject to provide the desired result of treatment (e.g., the elevation of Glutathione levels).

Figure 5:
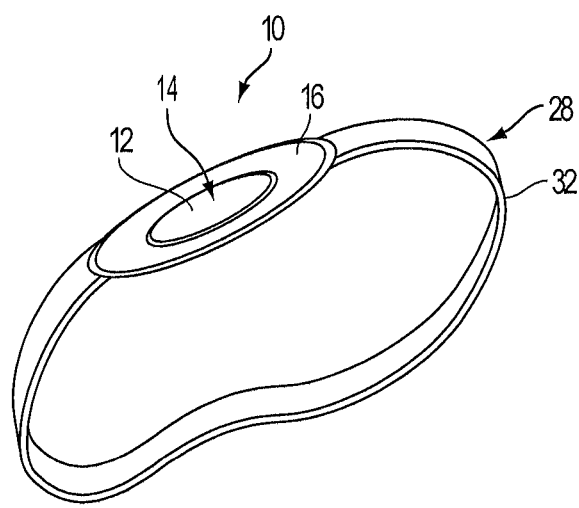
FIG. 5 illustrates an apparatus, according to one or more embodiments of the invention.

Although during treatment, apparatus 10 is placed at or near the subject, a variety of mechanisms that hold enclosure 16 in place at or near the skin of the subject may be implemented in place of the adhesive illustrated in FIG. 1. For example, FIG. 5 illustrates a band 32 that acts as mechanism 28 in that it carries enclosure 16 and is adapted to receive an extremity of the subject therethrough, thereby retaining enclosure 16 at or near the surface of the received extremity. In some implementations, band 32 may be disposable. In some implementations, band 32 may be reusable, and enclosure 16 may selectively replaceable on band 32. Band 32 may be a piece of jewelry, and may include one or more precious metals and/or precious or semi-precious stones for decorative purposes.

Figure 6:
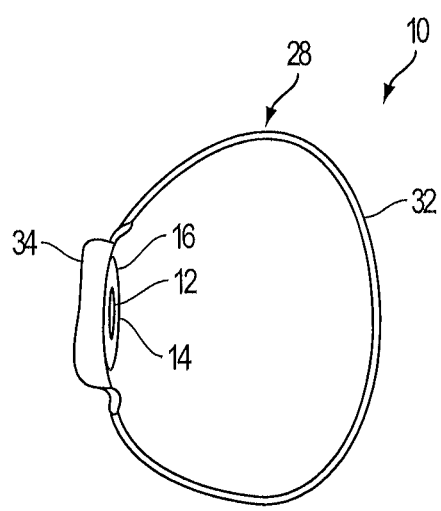
FIG. 6 illustrates an apparatus, according to one or more embodiments of the invention.

FIG. 6 illustrates one or more implementations of apparatus 10 in which band 32 is a watchband, and carries a watch face 34. Enclosure 16 may be selectively removable/replaceable from band 32.

Figure 7:
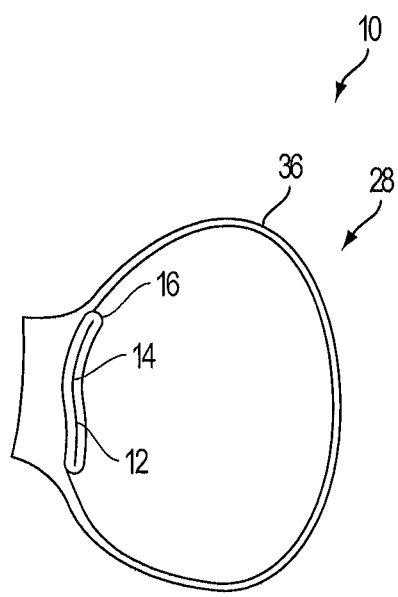
FIG. 7 illustrates an apparatus, according to one or more embodiments of the invention.

FIG. 7 illustrates one or more implementations of apparatus 10 in which a ring 36 acts as mechanism 28 in that it carries enclosure 16 and is adapted to receive a finger of the subject therethrough, thereby retaining enclosure 16 at or near the surface of the received finger. In some implementations, ring 36 may be disposable. In some implementations, ring 36 may be reusable, and enclosure 16 may selectively replaceable on ring 36. Ring 36 may be a piece of jewelry, and may include one or more precious metals and/or precious or semi-precious stones for decorative purposes.

It should be appreciated that the various implementations of mechanism 28 for affixing enclosure to the subject illustrated in FIGS. 1 and 5-7 are not intended to be limiting. Other implementations of mechanism 28 are also contemplated. For example, mechanism 28 may include an article of clothing (e.g., a sock, a shirt, shorts, shoe inserts, etc.), an article of jewelry other than those enumerated above (e.g., a necklace, a pendant, etc.), and/or other mechanisms capable of affixing enclosure 16 to the subject.

Treatment

As has been enumerated above, depleted Glutathione levels are a cause and/or symptom of various ailments. These ailments include conditions linked with elevated levels of mercury within the body, diabetes, degenerative brain conditions (e.g., Parkinson's disease), peripheral artery disease, autism, liver toxicity, sepsis, viral infection (e.g., herpes, hepatitis, HIV, etc.), pulmonary disease, acute pancreatitis, burn injuries, auto-immune dysfunction (e.g., rheumatoid arthritis, lupus, etc.), osteoarthritis, stroke, heart attack, and/or other ailments. As a result, the scope of this disclosure encompasses a method of treating a subject suffering from one or more of these ailments with apparatus 10. The treatment, which would result in an elevation in the levels of Glutathione within the subject by a therapeutically effective amount, among other things, may include affixing apparatus 10 to the subject such that the apparatus remains at or near the skin of the subject for a prolonged period of time. For example, this period of time may be at least about.

Similarly, Glutathione levels may be depressed by various medical treatments designed to treat an affliction of the subject. For example, treatments that may depress Glutathione levels may include pain medications such as acetaminophen, anesthetic pharmaceuticals, cancer treatments (e.g., chemotherapy, radiation therapy, etc.), and/or other treatments. As a result, the scope of this disclosure encompasses a method of treating a subject having received another medical treatment, the effects of which include depressed Glutathione levels, with apparatus 10. The treatment, which would result in an elevation in the levels of Glutathione within the subject by a therapeutically effective amount, among other things, may include affixing apparatus 10 to the subject such that the apparatus remains at or near the skin of the subject for a prolonged period of time. For example, this period of time may be at least about.

Another cause of reduced Glutathione levels within an individual include exposure to chemical agents present at times during warfare. These chemical agents may include weaponized chemical agents (e.g., Mustard gas, phosgene, etc.), chemical agents produced during the operation of machinery for the purposes of warfare (e.g., organofluoride polymers, etc.), and/or other chemical agents. Accordingly, the scope of this disclosure encompasses a method of treating a subject having been exposed to one or more chemical agents during the course of warfare, the effects of which include depressed Glutathione levels, with apparatus 10. The treatment, which would result in an elevation in the levels of Glutathione within the subject by a therapeutically effective amount, among other things, may include affixing apparatus 10 to the subject such that the apparatus remains at or near the skin of the subject for a prolonged period of time. For example, this period of time may be at least about.

The elevation of Glutathione levels within the subject may enhance the health of individuals in a variety of circumstances outside of those enumerated immediately above. For example, the elevation of Glutathione levels may be of benefit to the subject in recovering from exercise, dealing with exposure to loud and/or prolonged noise, aging, and/or other circumstances. Accordingly, the scope of this disclosure encompasses a method of treating a subject experiencing one or more circumstances that tend to decrease the overall health of the subject with apparatus 10. The treatment, which would result in an elevation in the levels of Glutathione within the subject by a therapeutically effective amount, among other things, may include affixing apparatus 10 to the subject such that the apparatus remains at or near the skin of the subject for a prolonged period of time. For example, this period of time may be at least about.

According to various implementations of one or more of the methods of treatment described above, affixing apparatus 10 to the subject may include affixing apparatus 10 to the subject such that chemical mixture 14 and/or substrate 12 are held within enclosure 16 proximate to one or more predetermined locations on the subject. For example, the one or more predetermined locations on the subject may include one or more positions on the body of the subject that have a positive electrical potential. The one or more predetermined locations on the subject may include one or more acupuncture points, such as, for instance, one or more Yang points. In some implementations, the one or more predetermined locations comprise the palm side of the right forearm of the subject, one the chest of the subject, under the navel of the subject, and/or other locations on the body of the subject.

In order to show the efficacy of the apparatus in maintaining Glutathione levels at a therapeutically beneficial level, a study may be conducted with a set of subjects. The subjects may be within a predetermined age bracket (e.g., 30-50 years), may be healthy (e.g., without known chronic diseases), with varying diets, sleep habits, work habits, and levels of activity. Blood samples may be collected and may be measured to provide baseline measurements of Glutathione and Glutathione metabolites in the blood of the subjects. These measurements may be obtained by high-performance liquid chromatography. These measurement may include one or more of whole blood Glutathione, plasma Glutathione, serum Glutathione, oxidized blood Glutathione, erythrocyte Glutathione, etc. Similarly, urine samples may be collected from the subjects and may be measured to provide baseline measurement of Glutathione metabolites and heavy-metals excreted in the urine of the subjects. The study may be double-blind, and a set of placebo apparatuses may be administered to a first set of the subjects (e.g., including only saline as the chemical mixture). As set of apparatuses as set forth above may be administered to the second set of subjects. Subjects may be instructed to apply the apparatuses for a predetermined period of time each day (e.g., 10 hours) for a treatment period of some predetermined period of days (e.g., 7 days). Blood and urine samples may be taken from subjects each day during the treatment period, and measurements of Glutathione, Glutathione metabolites, and heavy metals in the blood and urine samples corresponding to the baseline measurements may be taken. It is expected that during the treatment period, the subjects that have been administered the apparatus as disclosed herein will experience levels of Glutathione, Glutathione metabolites, and heavy metals that are elevated over their baseline by a greater amount than the subjects that have been administered placebo apparatuses. The elevation of levels of Glutathione, Glutathione metabolites, and heavy metals experienced by the subjects that have been administered the apparatus as disclosed herein will tend to be therapeutically significant (e.g., at least about 1.5× the baseline measurements, at least about 2× the baseline measurements, at least about 2.5× the baseline measurements, at least about 3× the baseline measurements, etc.).

In order to show the efficacy of the apparatus in maintaining Glutathione levels at a therapeutically beneficial level for subjects suffering from a Glutathione mediated condition, a study may be conducted with a set of subjects. The subjects may be within a predetermined age bracket (e.g., 30-50 years), may have the same or similar Glutathione mediated condition (e.g., elevated levels of mercury within the body, diabetes, degenerative brain conditions (e.g., Parkinson's disease), peripheral artery disease, autism, liver toxicity, sepsis, viral infection (e.g., herpes, hepatitis, HIV, etc.), pulmonary disease, acute pancreatitis, burn injuries, auto-immune dysfunction (e.g., rheumatoid arthritis, lupus, etc.), osteoarthritis, stroke, heart attack, and/or other Glutathione mediated conditions), with varying diets, sleep habits, work habits, and levels of activity. Blood samples may be collected and may be measured to provide baseline measurements of Glutathione and Glutathione metabolites in the blood of the subjects. These measurements may be obtained by high-performance liquid chromatography. These measurement may include one or more of whole blood Glutathione, plasma Glutathione, serum Glutathione, oxidized blood Glutathione, erythrocyte Glutathione, etc. Similarly, urine samples may be collected from the subjects and may be measured to provide baseline measurement of Glutathione metabolites and heavy-metals excreted in the urine of the subjects. The study may be double-blind, and a set of placebo apparatuses may be administered to a first set of the subjects (e.g., including only saline as the chemical mixture). As set of apparatuses as set forth above may be administered to the second set of subjects. Subjects may be instructed to apply the apparatuses for a predetermined period of time each day (e.g., 10 hours) for a treatment period of some predetermined period of days (e.g., 7 days). Blood and urine samples may be taken from subjects each day during the treatment period, and measurements of Glutathione, Glutathione metabolites, and heavy metals in the blood and urine samples corresponding to the baseline measurements may be taken. It is expected that during the treatment period, the subjects that have been administered the apparatus as disclosed herein will experience levels of Glutathione, Glutathione metabolites, and heavy metals that are elevated over their baseline by a greater amount than the subjects that have been administered placebo apparatuses. The elevation of levels of Glutathione, Glutathione metabolites, and heavy metals experienced by the subjects that have been administered the apparatus as disclosed herein will tend to be therapeutically significant (e.g., at least about 1.5× the baseline measurements, at least about 2× the baseline measurements, at least about 2.5× the baseline measurements, at least about 3× the baseline measurements, etc.).

In order to show the efficacy of the apparatus in maintaining Glutathione levels at a therapeutically beneficial level in conjunction with a medical treatment that tends to depress Glutathione levels, a study may be conducted with a set of subjects. The subjects may be within a predetermined age bracket (e.g., 30-50 years), may be currently receiving the same or similar medical treatment that tends to depress Glutathione levels (e.g., pain medications such as acetaminophen, anesthetic pharmaceuticals, cancer treatments (e.g., chemotherapy, radiation therapy, etc.), and/or other treatments that tend to depress Glutathione levels), with varying diets, sleep habits, work habits, and levels of activity. Blood samples may be collected and may be measured to provide baseline measurements of Glutathione and Glutathione metabolites in the blood of the subjects. These measurements may be obtained by high-performance liquid chromatography. These measurement may include one or more of whole blood Glutathione, plasma Glutathione, serum Glutathione, oxidized blood Glutathione, erythrocyte Glutathione, etc. Similarly, urine samples may be collected from the subjects and may be measured to provide baseline measurement of Glutathione metabolites and heavy-metals excreted in the urine of the subjects. The study may be double-blind, and a set of placebo apparatuses may be administered to a first set of the subjects (e.g., including only saline as the chemical mixture). As set of apparatuses as set forth above may be administered to the second set of subjects. Subjects may be instructed to apply the apparatuses for a predetermined period of time each day (e.g., 10 hours) for a treatment period of some predetermined period of days (e.g., 7 days). Blood and urine samples may be taken from subjects each day during the treatment period, and measurements of Glutathione, Glutathione metabolites, and heavy metals in the blood and urine samples corresponding to the baseline measurements may be taken. It is expected that during the treatment period, the subjects that have been administered the apparatus as disclosed herein will experience levels of Glutathione, Glutathione metabolites, and heavy metals that are elevated over their baseline by a greater amount than the subjects that have been administered placebo apparatuses. The elevation of levels of Glutathione, Glutathione metabolites, and heavy metals experienced by the subjects that have been administered the apparatus as disclosed herein will tend to be therapeutically significant (e.g., at least about 1.5× the baseline measurements, at least about 2× the baseline measurements, at least about 2.5× the baseline measurements, at least about 3× the baseline measurements, etc.).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of treating a subject, the method comprising:
    elevating Glutathione levels by a therapeutically effective amount by affixing an apparatus to the subject such that the apparatus remains at or near the skin of the subject for a prolonged period of time, wherein the apparatus comprises:
    (A) one or more substrates;
    (B) a chemical mixture disposed on or about the one or more substrates, the chemical mixture including one or more natural amino acids, wherein if the one or more substrates and the chemical mixture are brought proximate to the subject without directly contacting the subject, the proximity of the one or more substrates and the chemical mixture to the subject trigger and maintain an increase in Glutathione levels in the body of the subject; and
    (C) an enclosure that surrounds the one or more substrates and the chemical mixture and is configured to prevent the one or more substrates and/or the chemical mixture from coming into direct contact with and entering the body of the subject.

2. The method of claim 1, wherein the chemical mixture comprises Glutathione.

3. A method of treating a subject, the method comprising:
    treating a subject suffering from a Glutathione mediated condition including one or more of a pulmonary disease, a degenerative brain condition, a viral infection, a burn injury, acute pancreatitis, an immune dysfunction, exposure to a chemical weapon, an effect of mercury exposure, or diabetes by elevating Glutathione levels in the subject to a therapeutically effective level by affixing an apparatus to the subject such that the apparatus remains at or near the skin of the subject for a prolonged period of time, wherein the apparatus comprises:

(D) one or more substrates;

(E) a chemical mixture disposed on or about the one or more substrates, the chemical mixture including one or more natural amino acids, wherein if the one or more substrates and the chemical mixture are brought proximate to the subject without directly contacting the subject, the proximity of the one or more substrates and the chemical mixture to the subject trigger and maintain an increase in Glutathione levels in the body of the subject; and (F) an enclosure that surrounds the one or more substrates and the chemical mixture and is configured to prevent the one or more substrates and/or the chemical mixture from coming into direct contact with and entering the body of the subject.

4. The method of claim 3, wherein the chemical mixture comprises Glutathione.

5. The method of claim 3, wherein treating the subject suffering from a Glutathione mediated condition including one or more of a pulmonary disease, a degenerative brain condition, a viral infection, a burn injury, acute pancreatitis, an immune dysfunction, or diabetes comprises treating the subject for side effects of another treatment administered to the subject for one or more of a pulmonary disease, a degenerative brain condition, a viral infection, a burn injury, acute pancreatitis, an immune dysfunction, or diabetes.

6. The method of claim 3, wherein treating the subject for one or more of a pulmonary disease, a degenerative brain condition, a viral infection, a burn injury, acute pancreatitis, an immune dysfunction, or diabetes comprises elevating the Glutathione levels within the body of the subject.

* * * * *